United States Patent [19]

Bailey

[11] Patent Number: 4,598,082
[45] Date of Patent: Jul. 1, 1986

[54] ANTIMICROBIAL (N-1-OCTYL-4(1H)-PYRIDINYLIDINE)OCTANAMINE AND ACID ADDITION SALTS THEREOF AND METHODS OF USE AND COMPOSITIONS THEREOF

[75] Inventor: Denis M. Bailey, East Greenbush, N.Y.

[73] Assignee: Sterling Drug Inc., New York, N.Y.

[21] Appl. No.: 649,587

[22] Filed: Sep. 12, 1984

[51] Int. Cl.$^4$ ............... C07D 213/74; A61K 31/44
[52] U.S. Cl. ................................. 514/352; 546/304
[58] Field of Search .................. 546/304; 424/263; 514/352

[56] References Cited

U.S. PATENT DOCUMENTS 4,206,215 6/1980 Bailey .................................. 546/264

OTHER PUBLICATIONS

Merck Index, 9th Edition (1976) p. 254.
Landquist, Journal of the Chemical Society, Perkin Transactions I, No. 4, pp. 454–456, 1976.

Primary Examiner—Henry R. Jiles
Assistant Examiner—Dale A. Bjorkman
Attorney, Agent, or Firm—Theodore C. Miller; Paul E. Dupont; B. Woodrow Wyatt

[57] ABSTRACT

N-[1-(alkyl or arylmethyl)-4(1H)-pyridinylidine]-alkanamine and pharmaceutically acceptable acid addition salts thereof, for example, N-(1-octyl-4(1H)-pyridinylidine)octanamine monohydrochloride salt, which are useful as antimicrobial agents, especially on living tissues and nonliving surfaces and most especially against pathogenic dental microbes, and a process for preparation, methods of use and compositions thereof are disclosed.

8 Claims, No Drawings

ANTIMICROBIAL (N-1-OCTYL-4(1H)-PYRIDINYLIDINE)OCTANAMINE AND ACID ADDITION SALTS THEREOF AND METHODS OF USE AND COMPOSITIONS THEREOF

BACKGROUND OF THE INVENTION

1. Field of the Invention

The invention relates to N-[1-(alkyl or arylmethyl)-4(1H)-pyridinyline]alkanamines and acid addition salts thereof, which are useful as antimicrobial agents, especially on living tissues and nonliving surfaces and most especially against pathogenic dental microbes, and a process for preparation, methods of use and compositions thereof.

2. Information Disclosure Statement

Landquist (Journal of the Chemical Society, Perkin Transactions I, no. 4, pp. 454–456, 1976) describes the preparation of 1-methyl-4-methylaminopyridinium iodide and 4-dodecylamino-1-methylpyridinium iodide but does not describe or suggest any biological property thereof.

Bailey U.S. Pat. No. 4,206,215 issued June 3, 1980 describes antimicrobial bis[4-(substituted-amino)-1-pyridinium]alkane salts having the structural formula

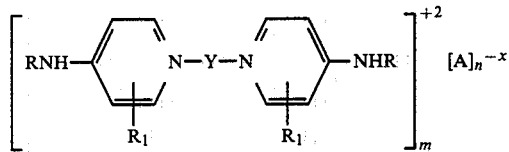

wherein:
Y is an alkylene group containing from 4 to 18 carbon atoms and separating the two 4-(R-NH)-1-pyridinyl groups by from 4 to 18 carbon atoms;
R is an alkyl group containing from 6 to 18 carbon atoms, a cycloalkyl group containing from 5 to 7 carbon atoms, benzyl, or phenyl substituted by methylenedioxy or one or two substituents selected from the group consisting of halogen, lower-alkyl, lower-alkoxy, nitro, cyano and trifluoromethyl;
$R_1$ is hydrogen or lower alkyl
A is an anion;
m is 1 or 3;
n is 1 or 2;
x is 1, 2 or 3; and
wherein
(m)(2)=(n)(x).

Parts A and B of Example 10 of this patent describe 1,10-bis[4-(octylamino)-1-pyridinium]decane dichloride, which can also be named N,N'-(1,10-decanediyldi-1(4H)-pyridinyl-4-ylidene)bis[1-octanamine]dihydrochloride, and whose generic name is octenidine hydrochloride.

SUMMARY OF THE INVENTION

In a first composition of matter aspect the invention is N-[1-(alkyl or arylmethyl)-4(1H)-pyridinylidene]alkanamine having the structural formula

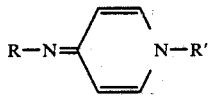

Formula I wherein
R is alkyl having from 6 to 18 carbon atoms; and
R' is alkyl having from 2 to 12 carbon atoms, phenylmethyl or halophenylmethyl; or
an acid addition salt thereof.

A particularly preferred composition of matter aspect of the invention is the compound of Formula I wherein R and R' are both octyl or a pharmaceutically acceptable acid addition salt thereof, which is the compound of Example 1 described below.

The compounds of Formula I and the acid addition salts thereof are useful as antimicrobial agents, especially on living tissues or nonliving surfaces and most especially against pathogenic dental microbes in primates.

In a first process aspect the invention is the method of reducing the number of microbes on a living tissue or a nonliving surface which comprises applying to the tissue or surface an antimicrobially effective amount of N-[1-(alkyl or arylmethyl)-4(1H)-pyridinylidene]alkanamine having the structural formula

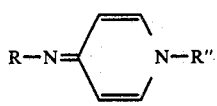

Formula II wherein
R is alkyl having from 6 to 18 carbon atoms; and
R'' is alkyl having from 1 to 12 carbon atoms, phenylmethyl or halophenylmethyl; or
an acid addition salt thereof.

In a second process aspect the invention is the process of preparing N-[1-(alkyl or arylmethyl)-4(1H)-pyridinylidene]alkanamine of Formula II or an acid addition salt thereof which comprises alkylating the corresponding 4-alkylaminopyridine having the structural formula

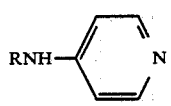

Formula III with the corresponding compound having the structural formula

  Formula IV

R''—X wherein X is a displaceable leaving group and isolating the HX acid addition salt, or if the acid addition salt is desired to be that of an acid other than HX isolating the desired acid addition salt by ion exchange, or isolating the free base or a mixture of the free base and the acid addition salt.

In a third process aspect the invention is the method of reducing the number of pathogenic dental microbes and associated dental plaque and gingivitis in a primate which comprises applying to the oral cavity of the primate an antimicrobially effective amount of N-[1-(alkyl or arylmethyl)-4(1H)-pyridinylidine]alkanamine of Formula II or a pharmaceutically acceptable acid addition salt thereof.

In a second composition of matter aspect the invention is an antimicrobial composition which comprises an antimicrobially effective concentration of N-[1-(alkyl or arylmethyl)-4-(1H)-pyridinylidene]alkanamine of Formula II or a pharmaceutically acceptable acid addition salt thereof and a compatible vehicle consisting of a diluent and one or more pharmaceutical adjuncts.

DETAILED DESCRIPTION OF THE INVENTION INCLUSIVE OF THE PREFERRED EMBODIMENTS

Definitions of the Variables

In the second process aspect of the invention "corresponding" means that R of Formula II and R of Formula III are the same and R" of Formula II and R" of Formula IV are the same.

R of Formulas I, II and III, which is alkyl having from 6 to 18 carbon atoms, is preferably primary alkyl, can be branched or unbranched, and is for example hexyl, heptyl, octyl, nonyl, dodecyl, tetradecyl, octadecyl or 2-ethylhexyl. Octyl is most preferred.

When R' of Formula I is alkyl of 2 to 12 carbon atoms, it is preferably primary alkyl, can be branched or unbranched, and is for example ethyl, propyl, butyl, pentyl, hexyl, heptyl, octyl, nonyl, dodecyl or 2-ethylhexyl. Octyl is most preferred. The preferences for R" of Formulas II and IV, which is alkyl of 1 to 12 carbon atoms, are the same except that it additionally includes methyl.

When R' of Formula I or R" of Formulas II and IV is halophenylmethyl, halo is fluoro, chloro, bromo or iodo. p-Halophenylmethyl is preferred. p-Chlorophenylmethyl is most preferred.

The acid addition salt of N-[1-(alkyl or arylmethyl)-4(1H)-pyridinylidene]alkanamine of Formula I or II can be that of any organic or inorganic acid which does not interfere with the antimicrobial effectiveness of the free base and has the structural formula

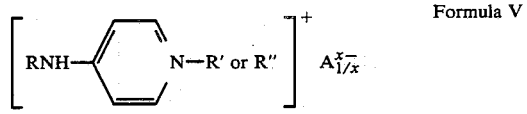

Formula V wherein A is an anion and x is the valence of the anion. Pharmaceutically acceptable acid addition salts are of course necessary in carrying out the pharmaceutical aspects of the invention.

The anion $A^{x-}$ is, for example, chloride, bromide, iodide, fluoride, sulfate, phosphate, monofluorophosphate, nitrate, sulfamate, methanesulfonate, ethanesulfonate, benzensulfonate, p-toluenesulfonate, naphthalenesulfonate, cyclohexylsulfonate, napthalenedisulfonate, cyclohexylsulfamate, acetate, trifluoroacetate, malate, fumarate, succinate, tartrate, tartronate, oxalate, citrate, lactate, gluconate, ascorbate, phthalate, silicylate, benzoate, picrate, methanephosphate, ethane-1-hydroxy-1,1-diphosphonate, thiosulfate, perchlorate, sarcosinate, N-lauroylsarcosinate, nitrilotriacetate, 2-hydroxyethylnitrilodiacetate, zinc phenolsulfonate, 1-oxo-2-pyridinethiolate, tetrafluoroborate, hexachloroplatinate, hexafluoroaluminate, tetrachloroaluminate, hexafluorostannate, hexafluorosilicate, fluorozirconate, laurylsulfate and saccharinate. Chloride, bromide and iodide are preferred. Chloride is most preferred.

The valence x of the anion $A^{x-}$ is most generally 1, 2 or 3. When $A^{x-}$ is chloride, for example, x is 1. When $A^{x-}$ is sulfate, for example, x is 2. When $A^{x-}$ is phosphate, for example, x is 3.

The displaceable leaving group X of R"—X of Formula IV generally has anionic character and may be the same as A and thus become the same as $A^{x-}$ after displacement. Chloride, bromide, iodide and readily available sulfonate ester groups, for example, methanesulfonate and p-toluenesulfonate are preferred. Chloride is most preferred.

Preparation of the Compounds

The synthetic intermediates of Formulas III and IV are known classes of compounds and are commercially available or can be made by methods specifically or generally described in the chemical literature. Those compounds of Formula III which are not commercially available can be made by heating at 200°–250° C. 4-chloropyridine or an acid addition salt thereof, especially the hydrochloride salt, with the corresponding alkylamine (RNH₂) or an acid addition salt thereof, especially the hydrochloride salt, and isolating the free base form of the product. The preferred compounds of Formula IV wherein X is chloro, bromo or iodo are generally commercially available.

Alkylation of the compounds of Formula III with the compounds of Formula IV is carried out with or without a solvent at a temperature in the range of 40°–250° C. The solvent can be any solvent or mixture of solvents which does not interfere with the alkylation and can be selected from the hydrocarbons, halohydrocarbons, alcohols, esters, amides, nitriles and other monofunctional solvents and the polyfunctional and mixed functional solvents. On small scale alkylation without a solvent is preferred. On large scale a solvent is necessary because the reaction is exothermic. The preferred solvent is isooctane(2,2,4-trimethylpentane).

It is generally preferred that the alkylation of the compound of Formula III with the compound of Formula IV produce the desired acid addition salt of the compound of Formula II directly, that is, that X of Formula IV be chosen so that X is the same as A of Formula V. The product of the alkylation is thus the acid addition salt of the free base form of the compound of Formula II with the acid HX. Those compounds of Formula V wherein A cannot be the same as X, that is, wherein A is not a displaceable leaving group and which therefore cannot be prepared by the alkylation process, can be prepared by known ion exchange methods, for example, by use of ion exchange resins or double displacement reactions.

The free base forms of the compounds of Formula II are preferably not isolated because they are difficult to separate from, and less stable than, the acid addition salt forms. Moreover, the acid addition salt forms are generally more desirable for pharmaceutical purposes.

The acid addition salt forms of the compounds of Formulas I and II, that is, the compounds of Formula V, are generally crystalline solids and are purified by recrystallization from appropriate solvents.

In the examples set forth below structures of products are inferred from structures of starting materials and expected courses of preparative reactions. Structural confirmation and estimation of purity of starting materials and products are measured by melting temperature range (m.r.), elemental analysis, infrared (IR) spectral analysis, ultraviolet (UV) spectral analysis, nuclear magnetic resonance (NMR) spectral analysis, gas chromatography (GC), high pressure liquid chromatography (HPLC) and thin layer chromatography (TLC).

Table I sets forth the melting ranges of the compounds of Formula III prepared by the method described above and used in the examples.

TABLE I

RNH—⟨pyridine⟩—N

| R | m.r. (C°.) |
|---|---|
| $CH_3(CH_2)_5$ | 63–65 |
| $CH_3(CH_2)_6$ | 43–45 |
| $CH_3(CH_2)_7$ | 58–61 |
| $CH_3(CH_2)_8$ | 53–56 |
| $CH_3(CH_2)_3(CH_3CH_2)CHCH_2$ | oil |
| $CH_3(CH_2)_{11}$ | 78–82 |

EXAMPLE 1

A. A mixture of 4-octylaminopyridine (10 g., 0.048 mole) and octyl bromide (8 ml., 0.048 mole) was heated at 125° C. for 8 hr. on one day and for 4 more hr. on the next day. The resulting solid was slurried, first in ether, then in ether-tetrahydrofuran (2:1) and finally in tetrahydrofuran, collected by filtration, washed with ether on the filter, and dried (70° C., 0.1 mm.) affording N-(1-octyl-4(1H)-pyridinylidene)octanamine monohydrobromide (11.95 g., 83% yield, m.r. 108°–112° C.), which is the monohydrobromide salt of the compound of Formula I wherein both R and R' are octyl.

B. A mixture of 4-octylaminopyridine (25 g., 0.121 mole) and octyl chloride (20.5 ml., 0.121 mole) was heated at 180° C. for 1 hr. More octyl chloride (0.5 ml.) was added and the mixture was again heated at 180° C. for 1 hr., then dissolved in dichloromethane. The dichloromethane solution was treated with charcoal, filtered, and stripped of solvent under vacuum. The solid residue was slurried in ether (1.5 kg.), collected by filtration, washed with ether (500 g.), isolated in a dry bag, and dried (50°–80° C., 0.1 mm.). The procedure was repeated using the same amounts of starting materials and the products were combined, affording N-(1-octyl-4(1H)-pyridinylidene)octanamine monohydrochloride (80.5 g., 93% yield, m.r. 120°–125° C.), which is the monohydrochloride salt of the compound of Formula I wherein R and R' are both octyl.

C. Octyl chloride (800 ml., 4.70 mole) was added to a solution of 4-octylaminopyridine (650 g., 3.16 mole) in warm (50° C.) isooctane (b.p. 99.3° C.). The resulting solution was heated under reflux. Crystals began to separate from the solution after 2 hr. Refluxing was continued for 36 hr. The solution was then allowed to cool to room temperature and filtered. The solid was washed with cold cyclohexane (1 l.) then slurried in hot (70° C.) cyclohexane (4 l.) for 0.5 hr. The slurry was allowed to cool to 60° C. and filtered. The solid (1050 g.) was slurried in boiling cyclohexane for 0.5 hr. The slurry was cooled to 50° C. and filtered. The solid was dried at 60° C. under vacuum, affording N-(1-octyl-4(1H)-pyridinylidine)octanamine monohydrochloride (1035 g., 92% yield, m.r. 140°–142° C.), which is a higher melting crystalline form of the product of part B of this example.

D. A filtered solution of N-(1-octyl-4(1H)-pyridinylidine)octanamine monohydrochloride salt (33.5 g.) in methanol (335 ml.) was added dropwise with stirring to a filtered solution of saccharin sodium salt (20.1 g.) in water (2.5 l.). The mixture was stirred for several hours, allowed to stand overnight and filtered. The resulting solid was washed with water, and dried, first on the filter and then at 30°–35° C. under high vacuum using a dry ice condenser, affording N-(1-octyl-4(1H)-pyridinylidine)octanamine monosaccharin salt (42.2 g., m.r. 65°–67° C.).

EXAMPLES 2–19

Examples 2–19 are summarized in Tables II and III. Table II shows the structural formulas of the products. Table III shows the reaction temperatures and yields and melting ranges of the products. When the reaction temperature was 125° C. or 130° C., the reaction time was about 12 hr. When the reaction temperature was 180° C., the reaction time was 1–3 hr. In all but Example 6, wherein the solvent was isoamyl alcohol, and Example 19, wherein the solvent was excess methyl iodide, the alkylations were carried out without solvent.

The compound of Example 19 is considered to be identical with the compound described as 4-dodecylamino-1-methylpyridinium iodide and as having been prepared from 4-cyano-1-methylpyridinium iodide and dodecylamine (m.r. 122°–124° C.) by the above-cited Landquist reference.

TABLE II

R—N=⟨ring⟩=N—R''.HX

| Example | R | R'' | X |
|---|---|---|---|
| 2 | $CH_3(CH_2)_6$ | $CH_3(CH_2)_6$ | Br |
| 3 | $CH_3(CH_2)_8$ | $CH_3(CH_2)_8$ | Cl |
| 4 | $CH_3(CH_2)_7$ | $CH_3(CH_2)_6$ | Br |
| 5 | $CH_3(CH_2)_7$ | $CH_3(CH_2)_8$ | Cl |
| 6 | $CH_3(CH_2)_5$ | $CH_3(CH_2)_5$ | Br[a] |
| 7 | $CH_3(CH_2)_7$ | $CH_3(CH_2)_3(CH_3CH_2)CHCH_2$ | Br |
| 8 | $CH_3(CH_2)_3(CH_3CH_2)CHCH_2$ | $CH_3(CH_2)_7$ | Br |
| 9 | $CH_3(CH_2)_6$ | $CH_3(CH_2)_8$ | Cl |
| 10 | $CH_3(CH_2)_7$ | $CH_3(CH_2)_5$ | Br |
| 11 | $CH_3(CH_2)_8$ | $CH_3(CH_2)_6$ | Br |
| 12 | $CH_3(CH_2)_8$ | $CH_3(CH_2)_7$ | Br |
| 13 | $CH_3(CH_2)_3(CH_3CH_2)CHCH_2$ | $CH_3(CH_2)_3(CH_3CH_2)CHCH_2$ | Br |
| 14 | $CH_3(CH_2)_6$ | $CH_3(CH_2)_7$ | Br |
| 15 | $CH_3(CH_2)_7$ | $C_6H_5CH_2$ | Cl |

TABLE II-continued $$R-N=\langle\rangle=N-R''\cdot HX$$

| Example | R | R'' | X |
|---|---|---|---|
| 16 | $CH_3(CH_2)_{11}$ | $C_6H_5CH_2$ | Cl |
| 17 | $CH_3(CH_2)_{13}$ | $C_6H_5CH_2$ | Cl |
| 18 | $CH_3(CH_2)_7$ | $4\text{-}ClC_6H_4CH_2$ | Cl |
| 19 | $CH_3(CH_2)_{11}$ | $CH_3$ | I |

[a] ⅔ HBr salt. HBr salt partly neutralized during workup.

TABLE III

| Example | Reaction Temperature °C. | Yield % | Melting Range °C. |
|---|---|---|---|
| 2 | 125 | 76 | 88–90 |
| 3 | 125 | 25 | 140–143 |
| 4 | 125 | 81 | 80–81 |
| 5 | 125 | 81 | 142–144 |
| 6 | 132[a] | 52 | 74–76 |
| 7 | 130 | 94 | 162–170 |
| 8 | 130 | 86 | 115–119 |
| 9 | 130 | 37 | 122 |
| 10 | 180 | 92 | 78–80 |
| 11 | 180 | 93 | 98–101 |
| 12 | 180 | 92 | 110–112 |
| 13 | 180 | 81 | 152–158 |
| 14 | 180 | 88 | 99–101 |
| 15 | 180 | 85 | 129–130 |
| 16 | 180 | 80 | 99–102 |
| 17 | 180 | 91 | 103–108 |
| 18 | 180 | 43 | 115–119 |
| 19 | 43[b] | 88 | 117–121 |

[a] Isoamyl alcohol solvent. Refluxed overnight.
[b] Excess methyl iodide solvent. Refluxed overnight.

ANTIMICROBIAL PROPERTIES OF THE COMPOUNDS

As stated above and in accordance with the first process aspect of the invention the compounds of Formulas I and II and the acid addition salts thereof are useful as antimicrobial agents, especially on living tissues or nonliving surfaces. This was demonstrated in the excised porcine skin disk immersion test against both resident and transient microflora.

In the test against resident microflora sterile excised porcine skin disks 10 mm. in diameter were inoculated with a *Klebsiella oxytoca* K-1 (Bender Hygienic Laboratory, Albany, N.Y.) or *Staphylococcus epidermidis* ATCC 17917 culture containing between $10^6$ and $10^7$ colony-forming units/ml., incubated in tryptose phosphate broth for 6 hr. at 37° C., separated from the both, reincubated for 18–24 hr. at 30° C., washed twice with aqueous 0.0743M potassium dihydrogen phosphate containing 0.1% of polyethylene glycol p-isooctylphenyl ether (Triton X-100 brand), and stored at −70° C. The disks were thawed prior to testing.

In the test against transient microflora sterile excised porcine skin disks were inoculated with 20 μl of a freshly prepared culture of *klebsiella oxytoca* K-1, *Escherichia coli* E-32, *Pseudomonas aeruginosa* Ps-4 (all from Bender Hygienic Laboratory, Albany, N.Y.) or *Staphylococcus aureus* ATCC 39881, then allowed to air dry for 15 min.

An inoculated disk was tested by immersing for 3 min. (resident microflora test) or 5 min. (transient microflora test) in 2 ml. of a 5 mM solution of the test compound in sterile distilled water or 25% aqueous dimethylsulfoxide or the solvent alone as a control solution, rinsing twice with sterile aqueous 25 mM potassium dihydrogen phosphate (pH 7.2), swirling for 30 sec. in tryptose phosphate broth modified to contain 0.8% polysorbate 80, 0.25% condensed naphthalene sulfonic acid sodium salt anionic dispersant (Tamol-N Micro brand), 0.1% lecithin and 0.1% sodium thiosulfate, and sampling.

To determine the number of surviving bacteria a sample was neutralized and 1.0 ml. aliquots of successive tenfold dilutions thereof in the modified tryptose phosphate broth were plated in duplicate with tryptic soy agar (DIFCO Laboratories, Detroit, Mich.) by the pour plate technique. The plates were incubated at 37° C. for 48–72 hr. and counted using an automated colony counter coupled with a computer for statistical analysis of the data. Mean log reductions of counts from controls and standard errors were determined.

Table IV shows the results of the resident microflora test using *Staphylococcus epidermidis* ATCC 17917. Table V shows the results of the transient microflora test using all four test microorganisms. Standard errors for controls were in all cases ±0.15 or less.

TABLE IV

Resident Microflora Test

| Example | Mean Log Reduction |
|---|---|
| 1A[b] | 0.51 ± 0.10 |
| 2[a] | 1.05 ± 0.23 |
| 3[a] | 0.44 ± 0.06 |
| 4[a] | 0.53 ± 0.11 |
| 6[a] | 1.26 ± 0.12 |
| 7[b] | 0.57 ± 0.14 |
| 8[b] | 0.56 ± 0.12 |
| 9[a] | 0.77 ± 0.12 |
| 10[a,c] | 0.88 ± 0.18 |
| 12[b] | 0.29 ± 0.18 |
| 13[b] | 0.72 ± 0.13 |
| 14[b] | 0.48 ± 0.15 |

[a] sterile distilled water
[b] 25% aqueous dimethylsulfoxide
[c] 8 disks

TABLE V

Transient Microflora Test

| | Mean Log Reduction | | | |
|---|---|---|---|---|
| Example | K. oxytoca | E. coli | Ps. aerug. | S. aureus |
| 1A[b] | 1.68 ± 0.26 | 1.20 ± 0.09 | 1.38 ± 0.12 | 1.21 ± 0.13 |
| 2[a] | 2.49 ± 0.20 | 1.37 ± 0.13 | 1.99 ± 0.08 | 1.01 ± 0.20 |
| 3[a] | 1.15 ± 0.36 | 1.07 ± 0.08 | 1.04 ± 0.06 | 0.87 ± 0.13 |
| 4[a] | 2.12 ± 0.35 | 1.52 ± 0.12 | 1.72 ± 0.09 | 1.19 ± 0.13 |
| 5[a] | 0.67 ± 0.14 | e | e | e |
| 6[a] | 1.90 ± 0.33 | 0.98 ± 0.08 | 1.66 ± 0.08 | 0.96 ± 0.13 |
| 7[b] | 1.65 ± 0.22[c] | 1.13 ± 0.14 | 1.14 ± 0.13 | 1.32 ± 0.11 |
| 8[b] | 1.11 ± 0.14[d] | 1.11 ± 0.15 | 1.56 ± 0.04 | 1.39 ± 0.11 |
| 9[a] | 1.98 ± 0.29 | 1.59 ± 0.14 | 1.62 ± 0.10 | 1.26 ± 0.20 |
| 10[a] | 1.74 ± 0.19 | 1.32 ± 0.12 | 1.78 ± 0.11 | 1.36 ± 0.15 |
| 11[b] | 0.59 ± 0.12 | e | e | e |
| 12[b] | 0.78 ± 0.18 | e | e | e |
| 13[b] | 1.34 ± 0.22 | 0.87 ± 0.07 | 1.22 ± 0.07 | 1.20 ± 0.11 |

TABLE V-continued

Transient Microflora Test

| | Mean Log Reduction | | | |
|---|---|---|---|---|
| Example | K. oxytoca | E. coli | Ps. aerug. | S. aureus |
| 14[b] | 1.82 ± 0.36 | 1.21 ± 0.09 | 1.27 ± 0.10 | 0.88 ± 0.07 |

[a] sterile distilled water
[b] 25% aqueous dimethylsulfoxide
[c] 8 disks
[d] 9 disks
[e] not tested As also stated above and in accordance with the third process aspect of the invention the compounds of Formulas I and II and the pharmaceutically acceptable acid addition salts thereof are most especially useful against pathogenic dental microbes and associated dental plaque and gingivitis in primates. This was demonstrated by tests in vitro against dental plaque forming bacteria and in vivo both prophylactically and therapeutically against plaque formation and gingival inflammation as manifestations of periodontal disease in the monkey.

In the in vitro dental plaque test *Streptococcus mutans* 6715-13 and *Actinomyces viscosus* M-100 were used as plaque-forming microorganisms. Cultures were stored prior to use in a frozen or lyophilized state and working stock cultures were maintained by twice monthly passage in fluid thioglycollate medium containing 20% (w/v) meat extract and excess calcium carbonate. For plaque formation a horse meat infusion medium containing 5% sucrose, 1% trypticase and 0.5% sodium chloride and having pH 7.1 (cf. Jordan et al., J. Dent. Res., vol. 39, pp. 116–123, 1960) was used. All cultures were adapted to this medium by at least one growth cycle prior to use in the test.

The test objects were clean, sterile ceramic hydroxylapatite (durapatite) slabs approximately 1 cm. × 1 cm. × 1 mm. in size, which were suspended by nichrome wire in medium containing the plaque-forming microorganism. The slabs were transferred to medium not containing the plaque-forming microorganism on each of the next two days. Media were maintained at 37° C. under an anaerobic atmosphere (85% $N_2$/10% $H_2$/5% $CO_2$). Slabs having plaques of similar size were used in each test.

A 1% (w/v) solution of each of the test compounds in 50% aqueous dimethylsulfoxide was prepared. This and four successive fivefold dilutions thereof in sterile distilled water (0.5%, 0.1%, 0.05%, 0.01%) were used as the test solutions.

A plaque-covered durapatite slab was immersed in 10 ml. of a test solution for 30 min. at 37° C., removed, twice rinsed by immersing in 15 ml. of sterile distilled water, then immersed in fresh medium containing the pH indicator bromocresol purple. Plaques were judged to be killed if acidity failed to form and turbidity failed to increase in the medium.

Table VI shows the results of this thirty-minute antiplaque test.

1-Methyl-4-methylaminopyridinium iodide (m.r. 224°–226° C.) was prepared from 4-cyano-1-methylpyridinium iodide and methylamine as described by the above-cited Landquist reference, tested in the thirty-minute antiplaque test, and found to be inactive at the 0.5% concentration.

TABLE VI

Thirty-Minute Antiplaque Test

| | Minimum Plaque-Killing Concentration (% w/v) | |
|---|---|---|
| Example | S. mutans 6715-13 | A. viscosus M-100 |
| 1A | 0.01 | 0.01 |
| 2 | 0.05 | 0.05 |
| 3 | 0.1 | 0.05 |
| 4 | 0.05 | 0.05 |
| 5 | 0.05 | 0.05 |
| 6 | 0.05 | 0.1 |
| 7 | 0.05 | 0.05 |
| 8 | 0.05 | 0.05 |
| 9 | 0.05 | 0.05 |
| 10 | 0.05 | 0.05 |
| 11 | 0.05 | 0.01 |
| 12 | 0.05 | 0.05 |
| 13 | 0.05 | 0.05 |
| 14 | 0.05 | 0.05 |
| 15 | 0.05 | 0.05 |
| 16 | 0.05 | 0.05 |
| 17 | 0.05 | 0.05 |
| 19 | 0.05 | 0.05 |

To simulate a person's daily use of a dentifrice or a mouthwash containing a compound of Formula I or II or a pharmaceutically acceptable acid addition salt thereof the same test was conducted by immersing the plaque-containing slab in the test solution for two minutes daily for as many days up to five as necessary to kill the plaque. If the plaque was not killed in five days, the test compound was still considered active if a higher concentration thereof killed the plaque in five days or less.

The results of this daily two-minute antiplaque test are expressed as a plaque bactericidal index (PBI) calculated by the equation PBI = concentration (mM) × 2 (min.) × number of days and are set forth in Table VII. The PBI values for the compound of part A of Example 1, for example, were calculated as follows:

PBI = 0.31 mM × 2 min. × 4 days = 2.5.

The approximately twofold difference between the PBI values for the compound of part A of Example 1, which is a hydrobromide salt, and the compound of parts B and C of Example 1, which is a hydrochloride salt, is not considered significant and is consistent with the belief that the antimicrobial properties of the compounds of Formulas I and II are independent of the salt forms.

However, significant differences were shown in the daily two-minute antiplaque test between the compound of Example 1 and two prior art compounds. Table VII shows that the compounds of parts A, B and C of Example 1 are from about 5 times to about 14 times more potent than the prior art compound of Example 19 in this test. Octenidine hydrochloride, which is the compound of parts A and B of Example 10 of above-cited U.S. Pat. No. 4,206,215, showed PBI values of 25.6 against *S. mutans* 6715-13 and 19.2 against *A. viscosus* M-100. The compounds of parts A, B and C of Example 1 are thus from about 8 times to about 18 times more potent than octenidine hydrochloride in the test.

The compounds of Examples 6 and 17 were not active in this test at concentrations of 6.32 mM and 5 mM, respectively, and were not tested at higher concentrations.

TABLE VII

Daily Two-Minute Antiplaque Test
Plaque Bactericidal Index (PBI)

| Example | S. mutans 6715-13 | A. viscosus M-100 |
|---|---|---|
| 1A | 2.5 | 2.5 |
| 1B,C | 1.4 | 1.4 |
| 2 | 8.0 | 5.4 |
| 3 | 10.4 | 5.2 |
| 4 | 7.8 | 7.8 |
| 5 | 13.3 | 13.3 |
| 7 | 12.5 | 12.5 |
| 8 | 10.0 | 10.0 |
| 9 | 8.4 | 10.4 |
| 10 | 10.8 | 13.5 |
| 11 | 10.0 | 10.0 |
| 12 | 9.7 | 9.7 |
| 13 | 20.0 | 20.0 |
| 14 | 10.4 | 10.4 |
| 15 | 30.0 | 12.0 |
| 16 | 15.4 | 10.3 |
| 19 | 12.4 | 19.2 |

Two tests of the compound of part A of Example 1 against plaque formation and gingival inflammation in the monkey were carried out, one prophylactic and the other therapeutic. Cynomolgus monkeys of both sexes having all of their permanent teeth and evidencing gingivitis were used, without pretreatment in the therapeutic test. In the prophylactic test the calculus and gingivitis were reduced by a combination of scaling and brushing with 0.2% aqueous chlorhexidine gluconate prior to treatment with the test compound. Three males and three females were used in each test group.

In each monkey the following four teeth their associated gingival areas were examined quantitatively for plaque and gingivitis: maxillary right first molar (1:6), maxillary left first premolar (2:4), mandibular left first molar (3:6), mandibular right first premolar (4:4). Plaque was assessed on the following scale: 0, no plaque on probe; 1, plaque on probe; 2, visible plaque; 3, heavy plaque. Gingivitis was assessed on the following scale: 0, absence of inflammation; 1, mild inflammation; 2, moderate inflammation; 3, severe inflammation. A plaque sample was taken from each of two monkeys of each test group and assessed for the following morphologic groups: coccoid, straight rods, filaments, fusiforms, curved plus motile forms. The number of microorganisims of each morphologic group was expressed as a percentage of the total cell number counted.

Positioned face down and under sedation each monkey was treated with 5 ml. of an aqueous solution of the test compound or of water alone as a control. One fourth of the 5 ml. amount was delivered to each quadrant. The excess was allowed to drain from the monkey's mouth.

In the prophylactic test the test solutions were 0.32 mM and 0.64 mM aqueous solutions of the compound of part A of Example 1 and a 3.2 mM aqueous solution of octenidine hydrochloride. Each monkey was treated once daily with the test solution for five consecutive days a week for three consecutive weeks. Plaque and gingivitis were scored on days 7, 14 and 21. Plaque samples for morphologic examination were taken on days 10, 17 and 24.

In the therapeutic test the test solutions were a 0.64 mM aqueous solution of the compound of part A of Example 1, 3.2 mM aqueous octenidine hydrochloride and 3.2 mM aqueous chlorhexidine gluconate. The test solutions were delivered into the gingival sulcus. Each monkey was treated once daily with the test solution for five consecutive days a week for two consecutive weeks. Plaque and gingivitis were scored on days 0, 7 and 15. Plaque samples for morphologic examination were taken on days 0, 3 and 10.

The results for the prophylactic test are shown in Tables VIII–X. Table VIII shows plaque scores, which are expressed as means per tooth with standard errors. Table IX shows gingivitis scores, which are also expressed as means per tooth with standard errors. Table X shows plaque morphology, which is expressed as the combined percentages of filaments, fusiforms and curved plus motile forms as a percentage of total forms assessed. These three forms are associated with plaque. The results for the therapeutic test are similarly shown in Tables XI–XIII.

The results of the prophylactic test show that all three test solutions significantly retarded redevelopment of gingivitis during the test period, the compound of part A of Example 1 5-10 times more effectively than octenidine hydrochloride. The results of the therapeutic test show that only the compound of part A of Example 1 effected significant reduction of gingivitis during the test period. Octenidine hydrochloride or chlorhexidine gluconate did not significantly cause disease remission under the test protocol.

TABLE VIII

Prophylactic Test
Mean Plaque Score

| Test Solution | Day 7 | Day 14 | Day 21 |
|---|---|---|---|
| Water | 0.48 ± 0.17 | 1.05 ± 0.13 | 1.30 ± 0.15 |
| Example 1A 0.32 mM | 0.49 ± 0.21 | 0.61 ± 0.21 | 0.94 ± 0.28 |
| Example 1A 0.64 mM | 0.28 ± 0.11 | 0.69 ± 0.20 | 0.76 ± 0.19 |
| Octenidine Hydrochloride 3.2 mM | 0.30 ± 0.08 | 0.42 ± 0.21 | 0.65 ± 0.21 |

TABLE IX

Prophylactic Test
Mean Gingivitis Score

| Test Solution | Day 7 | Day 14 | Day 21 |
|---|---|---|---|
| Water | 0.42 ± 0.14 | 1.24 ± 0.09 | 1.82 ± 0.08 |
| Example 1A 0.32 mM | 0.15 ± 0.015 | 0.40 ± 0.08 | 0.70 ± 0.12 |
| Example 1A 0.64 mM | 0.22 ± 0.08 | 0.46 ± 0.06 | 0.48 ± 0.08 |
| Octenidine Hydrochloride 3.2 mM | 0.36 ± 0.05 | 0.58 ± 0.1 | 0.71 ± 0.14 |

TABLE X

Prophylactic Test
% Plaque-Associated Morphologic Forms

| Test Solution | Day 10 | Day 17 | Day 24 |
|---|---|---|---|
| Water | 58.0 ± 2.3 | 68.4 ± 1.6 | 69 ± 1.8 |
| Example 1A 0.32 mM | 42.6 ± 4.8 | 20.6 ± 1.2 | 24.5 ± 3.6 |
| Example 1A 0.64 mM | 13.6 ± 2.9 | 12.8 ± 3.6 | 25 ± 3.6 |
| Octenidine Hydrochloride 3.2 mM | 27.5 ± 2.6 | 18.7 ± 2.9 | 24.6 ± 2.8 |

TABLE XI

| Test Solution | Therapeutic Test Mean Plaque Score | | |
|---|---|---|---|
| | Day 0 | Day 7 | Day 15 |
| Water | 1.21 ± 0.69 | 1.65 ± 0.1 | 1.59 ± 0.56 |
| Example 1A 0.64 mM | 1.53 ± 0.46 | 0.39 ± 0.26 | 0.42 ± 0.32 |
| Octenidine Hydrochloride 3.2 mM | 1.36 ± 0.53 | 0.49 ± 0.29 | 0.46 ± 0.37 |
| Chlorhexidine Gluconate 3.2 mM | 1.96 ± 0.57 | 0.94 ± 0.43 | 0.89 ± 0.50 |

TABLE XII

| Test Solution | Therapeutic Test Mean Gingivitis Score | | |
|---|---|---|---|
| | Day 0 | Day 7 | Day 15 |
| Water | 1.74 ± 0.33 | 2.21 ± 0.16 | 2.19 ± 0.34 |
| Example 1A 0.64 mM | 1.64 ± 0.14 | 1.08 ± 0.42 | 0.35 ± 0.16 |
| Octenidine Hydrochloride 3.2 mM | 1.79 ± 0.17 | 1.63 ± 0.18 | 1.36 ± 0.28 |
| Chlorhexidine Gluconate 3.2 mM | 1.97 ± 0.25 | 1.65 ± 0.15 | 1.06 ± 0.68 |

TABLE XIII

| Test Solution | Therapeutic Test % Plaque-Associated Morphologic Forms | | |
|---|---|---|---|
| | Day 0 | Day 3 | Day 10 |
| Water | 78.6 ± 3.6 | 58.7 ± 6.6 | 72.8 ± 5.3 |
| Example 1A 0.64 mM | 79.7 ± 4.1 | 10.3 ± 3.7 | 10.5 ± 3.9 |
| Octenidine Hydrochloride 3.2 mM | 77.3 ± 3.6 | 59.8 ± 4.6 | 38.2 ± 4.5 |
| Chlorhexidine Gluconate 3.2 mM | 78.0 ± 4.3 | 38.5 ± 4.6 | 45.6 ± 3.2 |

METHOD OF USE AND COMPOSITIONS

The first and third process aspects of the invention, which are methods of use of a compound of Formula II or an acid addition salt thereof, are generally carried out using an antimicrobial composition thereof in accordance with the second composition of matter aspect of the invention.

In the methods of use living tissue includes plant and animal tissue and animal tissue includes human tissue, especially the tissues of the oral cavity. Nonliving surfaces include hard and soft surfaces, especially those located or used where prevention of microbial transmission is desired. Hard surfaces include those of building interiors, furniture and equipment. Soft surfaces include those of paper and cloth, wet or dry.

In the compositions a compatible vehicle is one which does not interfere with the antimicrobial effectiveness of the compound of Formula II and comprises a diluent and one or more phrmaceutical adjuncts including surfactants, thickeners, buffers, emollients, preservatives, dyes, pigments, perfumes, flavors and other ingredients depending on the purposes of the compositions. The compositions include tinctures, lotions, ointments, creams, jellies, powders, surgical scrubs, skin cleansers, shampoos, soaps, dentifrices, mouthwashes, household and industrial disinfectants and cleansers and protective coatings and are prepared by conventional methods.

The preferred diluent is an aqueous or aqueous-alcoholic diluent. The preferred concentration of the compound of Formula II or the acid addition salt thereof is from about 0.01% to about 10% by weight/volume. Compositions of the compound of part C of Example 1 are particularly preferred, especially those for use in the oral cavity. The composition of EXample 20 is such a composition.

EXAMPLE 20

| Ingredient | % (Weight/Volume) |
|---|---|
| Compound of Example 1C | 0.025 |
| Sorbitol | 7.0 |
| Alcohol USP | 8.0 |
| Glycerin | 5.0 |
| Poloxamer 237 | 0.5 |
| Flavors | 0.1 |
| Dye | 0.0001 |
| Water to make | 100.0 |

I claim:

1. N-(1-Octyl-4(1H)-pyridinylidine)octanamine having the structural formula

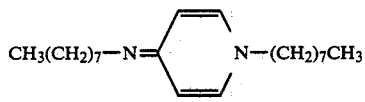

or a pharmaceutically acceptable acid addition salt thereof.

2. N-(1-Octyl-4(1H)-pyridinylidine)octanamine monohydrochloride salt according to claim 1.

3. N-(1-Octyl-4(1H)-pyridinylidine)octanamine monohydrobromide salt according to claim 1.

4. The method of reducing the number of pathogenic dental microbes and associated dental plaque and gingivitis in a primate which comprises applying to the oral cavity of the primate an antimicrobially effective amount of N-(1-octyl-4(1H)-pyridinylidine)octanamine having the structural formula

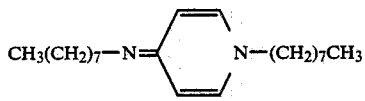

or a pharmaceutically acceptable acid addition salt thereof.

5. An antimicrobial composition which comprises an antimicrobially effective concentration of N-(1-octyl-4(1H)-pyridinylidine)octanamine having the structural formula

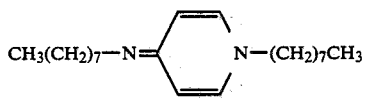

or a pharmaceutically acceptable acid addition salt thereof and a compatible vehicle consisting of a diluent and one or more pharmaceutical adjuncts.

6. A composition according to claim 5 wherein the concentration of N-(1-octyl-4(1H)-pyridinylidine)octanamine or a pharmaceutically acceptable acid addition salt thereof is from about 0.01% to about 10% by weight/volume.

7. A composition according to claim 6 wherein the diluent is an aqueous or aqueous-alcoholic diluent.

8. A composition according to claim 7 wherein the acid addition salt is the hydrochloride salt.

* * * * *